United States Patent
Menge et al.

(10) Patent No.: US 11,519,919 B2
(45) Date of Patent: Dec. 6, 2022

(54) ASSAY FOR THE DIAGNOSIS OF NEMATODE INFECTIONS

(71) Applicant: EUROIMMUN Medizinische Labordiagnostika AG, Luebeck (DE)

(72) Inventors: Babett Menge, Nahrendorf (DE); Katja Steinhagen, Gross Groenau (DE); Juliane Schaefer, OT Poehls (DE); Christian Probst, Ratzeburg (DE); Andrea Deerberg, Gross Groenau (DE); Mandy Unger, Hamburg (DE); Claudia Messing, Klempau (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 119 days.

(21) Appl. No.: 16/946,645

(22) Filed: Jun. 30, 2020

(65) Prior Publication Data

US 2021/0003591 A1     Jan. 7, 2021

(30) Foreign Application Priority Data

Jul. 2, 2019 (EP) .................................... 19183811

(51) Int. Cl.
| | | |
|---|---|---|
| *C12N 11/00* | (2006.01) | |
| *C12Q 1/00* | (2006.01) | |
| *G01N 33/53* | (2006.01) | |
| *G01N 33/567* | (2006.01) | |
| *G01N 33/569* | (2006.01) | |
| *G01N 33/68* | (2006.01) | |
| *C07K 14/435* | (2006.01) | |
| *C07K 16/18* | (2006.01) | |

(52) U.S. Cl.
CPC ..... *G01N 33/6893* (2013.01); *C07K 14/4354* (2013.01); *C07K 16/18* (2013.01); *G01N 2333/4353* (2013.01); *G01N 2800/26* (2013.01)

(58) Field of Classification Search
CPC ........................ C07K 14/4354; G01N 33/6893
See application file for complete search history.

(56) References Cited

FOREIGN PATENT DOCUMENTS

BR   102015026051    * 10/2020
BR   102015026051 A2 * 10/2020

OTHER PUBLICATIONS

Yamasaki et al., Parasitol. Int. 47:171-181(1998) (Year: 1998).*
Zhan et al., Trap Med Int Health, 2015; 20(12): 1787-96 (Year: 2015).*
Loukas et al., Parasitology 121:545-554(2000) (Year: 2000).*
Da Silva et al., Veterinary Parasitology, 2018; 259: 25-34 (Year: 2018).*
Bowie et al. (Science, 1990, 257:1306-1310) (Year: 1990).*
DCN Dx, Lateral Flow Immunoassays; Feb. 23, 2018; accessed from https://dcndx.com/lateral-flow-rapid-diagnostic-test/ (Year: 2018).*
Loukas et al., Current Biology, 1999; 9:825-828 (Year: 1999).*
Extended Search Report dated Jan. 22, 2020 in European Application 19183811.9, 10 pp.
Cottingham, Katie, Journal of Proteome Research; 2006, 5:5(1):1047-1048.
Jacquier et al., Journal of Clinical Microbiology; 1991, 29(9):1831-1835.
Jin, et al, Korean J Parasitol; 2013, 51(4):433-439.
Sugane et al., Molecular and Biochemical Parasitology; 1985, 14:275-281.
Ebrahimi et al., "Designing and Modeling of Multi-epitote Proteins for Diagnosis of *Toxocara canis* Infection", International Journal of Peptide Research and Therapeutics, vol. 26, 2020, pp. 1371-1380.

* cited by examiner

*Primary Examiner* — Gary B Nickol
*Assistant Examiner* — Lakia J Jackson-Tongue
(74) *Attorney, Agent, or Firm* — Grüneberg and Myers, PLLC

(57) ABSTRACT

A diagnostically useful carrier includes (a) a peptide including the amino acid sequence set forth in SEQ ID NO:1 or a variant thereof, and (b) a somatic lysate of *Toxocara canis* larvae. Further, a kit, use, methods, and compositions that include the diagnostically useful carrier are disclosed.

15 Claims, 5 Drawing Sheets

Specification includes a Sequence Listing.

Fig. 1

| No. | Sample type | TES-30 pos:≥ 0,350 OD | T. canis som. lysate pos:≥ 0,350 OD | T. canis TES antigens pos:≥ 0,350 OD | Combination of TES-30 and som. lysate pos:≥ 0,350 OD |
|---|---|---|---|---|---|
| 1 | pos. | 0,135 | 0,062 | 0,759 | 0,336 |
| 2 | pos. | 0,335 | 0,049 | 0,720 | 0,432 |
| 3 | pos. | 0,702 | 0,066 | 1,492 | 0,794 |
| 4 | pos. | 0,123 | 0,094 | 1,238 | 0,721 |
| 5 | pos. | 2,411 | 0,102 | 1,722 | 1,993 |
| 6 | pos. | 1,716 | 0,096 | 1,033 | 1,391 |
| 7 | pos. | 0,372 | 0,056 | 1,219 | 0,531 |
| 8 | pos. | 0,067 | 0,030 | 0,241 | 0,118 |
| 9 | pos. | 0,364 | 0,109 | 0,936 | 0,464 |
| 10 | pos. | 0,304 | 0,042 | 0,620 | 0,694 |
| 11 | pos. | 0,568 | 0,069 | 1,147 | 0,592 |
| 12 | pos. | 1,259 | 0,132 | 1,460 | 1,228 |
| 13 | pos. | 0,266 | 0,062 | 0,699 | 0,410 |
| 14 | pos. | 0,095 | 0,028 | 0,262 | 0,176 |
| 15 | pos. | 1,202 | 0,092 | 1,393 | 1,129 |
| 16 | pos. | 0,393 | 0,161 | 1,348 | 0,786 |

Fig. 2

| No. | Sample type | TES-30 pos:≥ 0,350 OD | *T. canis* som. lysate pos:≥ 0,350 OD | *T. canis* TES antigens pos:≥ 0,350 OD | Combination of TES-30 and som. lysate pos:≥ 0,350 OD |
|---|---|---|---|---|---|
| 17 | neg. | 0,050 | 0,037 | 0,672 | 0,212 |
| 18 | neg. | 0,026 | 0,017 | 0,396 | 0,108 |
| 19 | neg. | 0,071 | 0,016 | 0,288 | 0,108 |
| 20 | neg. | 0,051 | 0,078 | 0,522 | 0,170 |
| 21 | neg. | 0,218 | 0,046 | 0,370 | 0,252 |
| 22 | neg. | 0,063 | 0,016 | 0,211 | 0,106 |
| 23 | neg. | 0,100 | 0,035 | 0,714 | 0,201 |
| 24 | neg. | 0,232 | 0,037 | 0,572 | 0,234 |
| 25 | neg. | 0,080 | 0,023 | 0,294 | 0,091 |
| 26 | neg. | 0,055 | 0,070 | 0,159 | 0,141 |
| 27 | neg. | 0,045 | 0,015 | 0,112 | 0,071 |
| 28 | neg. | 0,037 | 0,011 | 0,064 | 0,055 |
| 29 | neg. | 0,036 | 0,011 | 0,062 | 0,055 |
| 30 | neg. | 0,027 | 0,005 | 0,049 | 0,024 |
| 31 | neg. | 0,066 | 0,013 | 0,143 | 0,094 |
| 32 | neg. | 0,059 | 0,028 | 0,101 | 0,103 |
| 33 | neg. | 0,119 | 0,008 | 0,048 | 0,104 |
| 34 | neg. | 0,049 | 0,010 | 0,049 | 0,036 |
| 35 | neg. | 0,051 | 0,009 | 0,055 | 0,073 |
| 36 | neg. | 0,055 | 0,012 | 0,071 | 0,097 |
| 37 | neg. | 0,047 | 0,019 | 0,128 | 0,126 |
| 38 | neg. | 0,082 | 0,006 | 0,037 | 0,051 |
| 39 | neg. | 0,081 | 0,018 | 0,108 | 0,114 |
| 40 | neg. | 0,031 | 0,005 | 0,019 | 0,032 |
| 41 | neg. | 0,017 | 0,002 | 0,009 | 0,007 |
| 42 | neg. | 0,021 | 0,008 | 0,040 | 0,038 |
| 43 | neg. | 0,027 | 0,006 | 0,074 | 0,036 |
| 44 | neg. | 0,214 | 0,023 | 0,159 | 0,219 |
| 45 | neg. | 0,035 | 0,005 | 0,034 | 0,025 |
| 46 | neg. | 0,022 | 0,004 | 0,023 | 0,042 |
| 47 | neg. | 0,039 | 0,009 | 0,061 | 0,060 |
| 48 | neg. | 0,029 | 0,010 | 0,036 | 0,036 |
| 49 | neg. | 0,036 | 0,039 | 0,210 | 0,113 |
| 50 | neg. | 0,036 | 0,008 | 0,022 | 0,525 |
| 51 | neg. | 0,083 | 0,023 | 0,536 | 0,136 |
| 52 | neg. | 0,035 | 0,005 | 0,025 | 0,035 |
| 53 | neg. | 0,043 | 0,011 | 0,125 | 0,046 |
| 54 | neg. | 0,046 | 0,010 | 0,131 | 0,101 |
| 55 | neg. | 0,023 | 0,003 | 0,056 | 0,012 |
| 56 | neg. | 0,033 | 0,007 | 0,074 | 0,060 |

| 57 | neg. | 0,053 | 0,096 | 1,000 | 0,656 |
| 58 | neg. | 0,087 | 0,013 | 0,142 | 0,082 |
| 59 | neg. | 0,118 | 0,052 | 0,579 | 0,306 |
| 60 | neg. | 0,037 | 0,012 | 0,036 | 0,047 |
| 61 | neg. | 0,046 | 0,045 | 0,079 | 0,068 |
| 62 | neg. | 0,061 | 0,027 | 0,087 | 0,083 |
| 63 | neg. | 0,098 | 0,020 | 0,111 | 0,106 |
| 64 | neg. | 0,026 | 0,008 | 0,031 | 0,024 |

| No. | Sample type | TES-30 pos:≥ 0,350 OD | T. canis som. lysate pos:≥ 0,350 OD | T. canis TES antigens pos:≥ 0,350 OD | Combination of TES-30 and som. lysate pos:≥ 0,350 OD |
|---|---|---|---|---|---|
| 65 | Ascaris | 0,059 | 0,022 | 0,454 | 0,120 |
| 66 | Ascaris | 0,035 | 0,018 | 0,109 | 0,107 |
| 67 | Ascaris | 0,078 | 0,027 | 0,243 | 0,160 |
| 68 | Ascaris | 0,035 | 0,007 | 0,042 | 0,066 |
| 69 | Ascaris | 0,040 | 0,012 | 0,080 | 0,063 |
| 70 | Ascaris | 0,033 | 0,006 | 0,022 | 0,020 |
| 71 | Ascaris | 0,035 | 0,030 | 0,231 | 0,170 |
| 72 | Ascaris | 0,043 | 0,023 | 0,024 | 0,054 |
| 73 | Ascaris | 0,016 | 0,005 | 0,024 | 0,019 |
| 74 | Ascaris | 0,021 | 0,013 | 0,089 | 0,034 |
| 75 | Ascaris | 0,032 | 0,023 | 0,402 | 0,133 |
| 76 | Ascaris | 0,022 | 0,008 | 0,023 | 0,040 |
| 77 | Ascaris | 0,109 | 0,034 | 0,299 | 0,161 |
| 78 | Ascaris | 0,154 | 0,025 | 0,396 | 0,204 |
| 79 | Ascaris | 0,037 | 0,018 | 0,273 | 0,147 |
| 80 | Ascaris | 0,048 | 0,027 | 0,149 | 0,110 |
| 81 | Ascaris | 0,094 | 0,035 | 0,558 | 0,310 |
| 82 | Echinokokkus | 0,065 | 0,020 | 0,196 | 0,104 |
| 83 | Echinokokkus | 0,029 | 0,068 | 0,051 | 0,101 |
| 84 | Echinokokkus | 0,042 | 0,027 | 0,072 | 0,064 |
| 85 | Echinokokkus | 0,244 | 0,054 | 0,182 | 0,215 |
| 86 | Echinokokkus | 0,091 | 0,060 | 0,353 | 0,189 |
| 87 | Echinokokkus | 0,032 | 0,010 | 0,052 | 0,075 |
| 88 | Echinokokkus | 0,027 | 0,010 | 0,039 | 0,046 |
| 89 | Echinokokkus | 0,102 | 0,024 | 0,108 | 0,141 |
| 90 | Echinokokkus | 0,027 | 0,016 | 0,495 | 0,133 |
| 91 | Strongyloides | 0,124 | 0,024 | 0,093 | 0,114 |
| 92 | Strongyloides | 0,033 | 0,041 | 0,099 | 0,085 |
| 93 | Strongyloides | 0,021 | 0,014 | 0,072 | 0,054 |
| 94 | Strongyloides | 0,048 | 0,014 | 0,063 | 0,083 |
| 95 | Strongyloides | 0,252 | 0,052 | 1,366 | 0,478 |
| 96 | Strongyloides | 0,099 | 0,028 | 2,373 | 0,144 |

Fig. 4 a)

| 16 pos. samples | results without vague samples | sensitivity [%] |
|---|---|---|
| TES-30 | 9/13 | 69,2 |
| *T. canis* som. lysate | 0/16 | 0,0 |
| *T. canis* TES antigens | 14/15 | 93,3 |
| Combination of TES-30 and som. lysate | 13/15 | 86,7 | b)

| 48 neg. samples | results without vague samples | specificity [%] |
|---|---|---|
| TES-30 | 48/48 | 100 |
| *T. canis* som. lysate | 48/48 | 100 |
| *T. canis* TES antigens | 35/46 | 72,9 |
| Combination of TES-30 and som. lysate | 44/46 | 95,7 | c)

| 32 neg. samples (other infections) | results without vague samples | specificity (parasitosis) [%] |
|---|---|---|
| TES-30 | 31/31 | 100 |
| *T. canis* som. lysate | 32/32 | 100 |
| *T. canis* TES antigens | 22/30 | 73,3 |
| Combination of TES-30 and som. lysate | 30/31 | 96,8 | d)

| | sensitivity [%] | specificity [%] | specificity (parasitosis) [%] | combined score |
|---|---|---|---|---|
| TES-30 | 69,2 | 100 | 100 | 269,2 |
| *T. canis* som. lysate | 0,0 | 100 | 100 | 200,0 |
| *T. canis* TES antigens | 93,3 | 72,9 | 73,3 | 239,5 |
| Combination of TES-30 and som. lysate | 86,7 | 95,7 | 96,8 | 280,3 |

SEQUENCE LISTING

<160> NUMBER OF SEQ ID NOS: 4

<210> SEQ ID NO 1
<211> LENGTH: 219
<212> TYPE: PRT
<213> ORGANISM: Toxocara canis

<400> SEQUENCE: 1

Met Ile Ala Ala Ile Val Val Leu Leu Cys Leu His Leu Ser Ala Thr

```
                1               5                    10                        15
            Asn Ala Cys Ala Thr Asn Asn Asp Cys Gly Ile Phe Gln Val Cys Val
                                20                      25                      30
            Asn Asn Val Cys Val Ala Asn Asn Gln Gly Cys Asn Pro Pro Cys Val
                                35                      40                      45
            Ala Pro Gln Val Cys Val Ala Pro Met Cys Val Ala Pro Pro Ala
                50                      55                      60
            Ala Thr Thr Thr Ala Ala Pro Gly Val Thr Thr Thr Arg Pro Arg Ala
            65                      70                      75                      80
            Cys Pro Pro Asn Trp Thr Pro Phe Asn Asn Cys Tyr Ile Ala Ser
                                85                      90                      95
            Leu Pro Gly Arg Phe Leu Phe Asn Gln Ala Ser Asp Trp Cys Thr Gln
                                100                     105                     110
            Thr Gly Ser Arg Val Val Trp Phe Asp Gln Ser Thr Val Gly Asn Phe
                                115                     120                     125
            Gly Ser Glu Leu Asn Phe Val Asn Ser Phe Ala Val Gly Arg Gly Val
                130                     135                     140
            Thr Arg Tyr Trp Ile Gly Val Asn Arg Gln Phe Gly Gln Trp Val Phe
            145                     150                     155                     160
            Thr Asn Gly Ser Pro Val Ile Phe Ser Asn Trp Arg Pro Ser Gln Pro
                                165                     170                     175
            Asp Gly Cys Cys Gly Ser Asn Val Thr Cys Ala Phe Val Asn Tyr Ala
                                180                     185                     190
            Asn Phe Leu Gly Gln Trp Asp Asp Ala Pro Cys Gly Ser Leu Phe Thr
                                195                     200                     205
            Thr Pro Gln Gly Phe Val Cys Lys Arg Pro Leu
                210                     215

<210> SEQ ID NO 2
<211> LENGTH: 230
<212> TYPE: PRT
<213> ORGANISM: Artificial Sequence
<220> FEATURE:
<223> OTHER INFORMATION: Toxocara canis TES-30 His-Tag

<400> SEQUENCE: 2

Met Ser His His His His His His His Ser Met Ile Ala Ala Ile
            1               5                    10                        15
            Val Val Leu Leu Cys Leu His Leu Ser Ala Thr Asn Ala Cys Ala Thr
                                20                      25                      30
            Asn Asn Asp Cys Gly Ile Phe Gln Val Cys Val Asn Asn Val Cys Val
                                35                      40                      45
            Ala Asn Asn Gln Gly Cys Asn Pro Pro Cys Val Ala Pro Gln Val Cys
                50                      55                      60
            Val Ala Pro Met Cys Val Ala Pro Pro Ala Ala Thr Thr Thr Ala
            65                      70                      75                      80
            Ala Pro Gly Val Thr Thr Thr Arg Pro Arg Ala Cys Pro Pro Asn Trp
                                85                      90                      95
            Thr Pro Phe Asn Asn Cys Tyr Ile Ala Ser Leu Pro Gly Arg Phe
                                100                     105                     110
            Leu Phe Asn Gln Ala Ser Asp Trp Cys Thr Gln Thr Gly Ser Arg Val
                                115                     120                     125
            Val Trp Phe Asp Gln Ser Thr Val Gly Asn Phe Gly Ser Glu Leu Asn
                130                     135                     140
            Phe Val Asn Ser Phe Ala Val Gly Arg Gly Val Thr Arg Tyr Trp Ile
```

-continued

```
                145                 150                 155                 160
Gly Val Asn Arg Gln Phe Gly Gln Trp Val Phe Thr Asn Gly Ser Pro
                    165                 170                 175

Val Ile Phe Ser Asn Trp Arg Pro Ser Gln Pro Asp Gly Cys Cys Gly
                180                 185                 190

Ser Asn Val Thr Cys Ala Phe Val Asn Tyr Ala Asn Phe Leu Gly Gln
            195                 200                 205

Trp Asp Asp Ala Pro Cys Gly Ser Leu Phe Thr Thr Pro Gln Gly Phe
        210                 215                 220

Val Cys Lys Arg Pro Leu
225                 230

<210> SEQ ID NO 3
<211> LENGTH: 51
<212> TYPE: PRT
<213> ORGANISM: Artificial Sequence
<220> FEATURE:
<223> OTHER INFORMATION: Toxocara canis TES-30 fragment 52 to 102 aa

<400> SEQUENCE: 3

Val Cys Val Ala Pro Met Cys Val Ala Pro Pro Ala Ala Thr Thr
1               5                   10                  15

Thr Ala Ala Pro Gly Val Thr Thr Thr Arg Pro Arg Ala Cys Pro Pro
                20                  25                  30

Asn Trp Thr Pro Phe Asn Asn Asn Cys Tyr Ile Ala Ser Leu Pro Gly
            35                  40                  45

Arg Phe Leu
    50

<210> SEQ ID NO 4
<211> LENGTH: 36
<212> TYPE: PRT
<213> ORGANISM: Artificial Sequence
<220> FEATURE:
<223> OTHER INFORMATION: Toxocara canis TES-30 fragment 172 to 207 aa

<400> SEQUENCE: 4

Arg Pro Ser Gln Pro Asp Gly Cys Cys Gly Ser Asn Val Thr Cys Ala
1               5                   10                  15

Phe Val Asn Tyr Ala Asn Phe Leu Gly Gln Trp Asp Asp Ala Pro Cys
                20                  25                  30

Gly Ser Leu Phe
        35
```

ASSAY FOR THE DIAGNOSIS OF NEMATODE INFECTIONS

CROSS-REFERENCE TO RELATED APPLICATION

The present application claims the benefit to European application EP 19 183 811.9, filed on Jul. 2, 2019, the content of which is hereby incorporated by reference in its entirety.

REFERENCE TO A SEQUENCE LISTING

The present application is accompanied by an ASCII text file as a computer readable form containing the sequence listing, titled "2020-06-29 Sequence Listing as filed.txt", created on Jun. 29, 2020, with the file size of 5,316 bytes, the content of which is hereby incorporated by reference in its entirety.

BACKGROUND OF THE INVENTION

Field of the Invention

The present invention relates to a diagnostically useful carrier comprising (a) a peptide comprising the amino acid sequence set forth in SEQ ID NO:1 or a variant thereof, and (b) a somatic lysate of *Toxocara canis* larvae. Further the present invention relates to a kit, use, methods, compositions comprising in the diagnostically useful carrier of the invention.

Discussion of the Background

Toxocariasis is a helminth infection of human which is caused by roundworm, *Toxocara canis* or *Toxocara cati*. This infection occurs when embryonated eggs containing fully developed infective larvae of the *Toxocara* spp. are ingested. The larvae in the human intestine will penetrate the bowel wall and migrate through blood vessels to reach liver, muscles and lungs, even migrating into the eye and brain.

Toxocariasis is often called visceral larva migrans (VLM). Alternative names or related symptoms may be ocular larva migrans (OLM), Weingarten's disease, Frimodt-Møller's syndrome or eosinophilic pseudoleukemia, nematode ophthalmitis, toxocaral disease, toxocarose or covert toxocariasis. This zoonotic, helminthic infection is a rare cause of blindness and may provoke rheumatic, neurologic, or asthmatic symptoms [Schantz, P M (1994). Journal of the American Veterinary Medical Association: 204 (7): 1023-8]. Humans normally become infected by ingestion of embryonated eggs (each containing a fully developed larva, L2) from contaminated sources (soil, undercooked meat, fresh or unwashed vegetables.).

*Toxocara canis* is a nematode whose basic life cycle consists of seven stages, an egg, four larval stages (L2, L2, L3, L4) and two adult stages comprising separate males and females. Nematodes molt four times during the larval stages with a molt occurring at the end of each larval stage.

As methods for the diagnosis and detection of toxocariasis are crucial for its prevention and treatment, several PCR, western-blot and ELISA based detection assays are disclosed in the art. Nonetheless, PCR assays require higher skilled personal and more expensive equipment. This can be limiting factors, especially in countries where seroprevalence to *Toxocara* is higher.

Thus, the diagnosis relies upon sensitive immunological methods (such as ELISA and western-blot) which use *Toxocara* excretory-secretory antigens. However, current immunological *Toxocara* assays do not provide high specificity and sensitivity at the same time. Examples of such assays are disclosed by dos Santos et al. [dos Santos et al. (2019), PLoS One: 14 (3)], Jin et al. [Jin et al. (2013), Korean J Parasitol: 51 (4): 433-9], Mohamad et al. [Mohamad et al. (2009), J Clin Microbiol: 47 (6): 1712-7] and Norhaida et al. [Norhaida et al. (2008), Ann Trop Med Parasitol; 102 (2): 151-60].

Therefore, there is a long-standing need for the provision of a serological assay for the combined sensitive and specific diagnosis of *Toxocara* infections.

SUMMARY OF THE INVENTION

The present application includes the following embodiments:
1. A diagnostically useful carrier comprising
   a) a peptide comprising the amino acid sequence set forth in SEQ ID NO:1 or a variant thereof, and
   b) a somatic lysate of *Toxocara canis* larvae.
2. The diagnostically useful carrier according to embodiment 1, wherein the peptide and the lysate are conjointly combined.
3. The diagnostically useful carrier according to embodiment 1 or 2, wherein the carrier is selected from the group comprising a glass slide, a biochip, a microtiter plate, a lateral flow device, a test strip, a membrane, a line blot, a chromatography column and a bead.
4. A kit comprising the diagnostically useful carrier according to embodiments 1 to 3 and a labeled antibody for detecting a human, Canidae or Rodentia antibody.
5. A method for diagnosing a *Toxocara* infection comprising detecting in a sample of a patient the presence of an antibody to SEQ ID NO:1 and/or an antibody to a somatic lysate of *Toxocara canis* larvae.
6. A composition comprising
   a) a peptide comprising the amino acid sequence set forth in SEQ ID NO:1 or a variant thereof, and
   b) a somatic lysate of *Toxocara canis* larvae.
7. A composition according to embodiment 6 or the diagnostically useful carrier according to embodiments 1 to 3 for use in the diagnosis of a *Toxocara* infection.
8. Method of determining the presence of an antibody against a *Toxocara canis* protein according to SEQ ID NO:1 and/or an antibody against a protein from a somatic lysate of *Toxocara canis* larvae, comprising
   i) contacting a sample isolated from a subject having a *Toxocara* infection with a polypeptide comprising SEQ ID NO:1 and/or a variant thereof and with a somatic lysate of *Toxocara canis* larvae, wherein the polypeptide and/or the lysate binds specifically to antibodies binding to SEQ ID NO:1 or the somatic lysate; and
   ii) determining the presence of an antibody against SEQ ID NO:1 and/or an antibody against the somatic lysate.
9. Use of a *Toxocara canis* protein according to SEQ ID NO:1 and a somatic lysate of *Toxocara canis* larvae for the manufacture of a kit for detecting *Toxocara* infection comprising
   a) a peptide comprising the amino acid sequence set forth in SEQ ID NO:1 or a variant thereof, and
   b) a somatic lysate of *Toxocara canis* larvae.
10. The method according to embodiment 5, the composition or carrier for use according to embodiment 7, the method according to embodiment 8 or the use according to embodiment 9, wherein the *Toxocara* infection is a *Toxocara canis* infection.

11. The method according to embodiment 5 or 8, wherein the sample is blood, serum, plasma, urine or saliva.
12. The method according to embodiment 5, the composition or carrier for use according to embodiment 7 or the use according to embodiment 9, wherein the *Toxocara* infection can be distinguished from an *Echinococcus*, a *Strongyloides* and an *Ascaris* infection.
13. The method according to embodiment 8 or the use according to embodiment 9, wherein the peptide and the lysate are conjointly combined.
14. The method according to embodiment 5 or the method according to embodiment 8, wherein the antibody against SEQ ID NO:1 and/or the antibody against the somatic lysate is selected from the group comprising IgG, IgA and IgM class antibodies.
15. The method according to embodiment 5, the method according to embodiment 8 or the use according to embodiment 9, wherein the detection or determination comprises a blot assay, chemiluminescence immunoassay, light scattering immunoassay, radiolabeled immunoassay or immunofluorescence assay.

BRIEF DESCRIPTION OF THE DRAWINGS

FIG. 1 shows results of different ELISAs using *T. canis* TES-30, somatic lysate *T. canis* larvae, *T. canis* excretory-secretory (TES) antigens and the combination of TES-30 and somatic larvae lysate for detection of *Toxocara* binding antibodies in samples of patients suffering from a *Toxocara* infection. Statistically significant positive detection results are shown in bold. Vague results are underlined.

FIG. 2 shows results of different ELISAs using *T. canis* TES-30, somatic lysate *T. canis* larvae, *T. canis* excretory-secretory (TES) antigens and the combination of TES-30 and somatic larvae lysate for detection of *Toxocara* binding antibodies in samples of a healthy control group. Statistically significant positive detection results are shown in bold. Vague results are underlined.

FIG. 3 shows results for different ELISAs using *T. canis* TES-30, somatic lysate *T. canis* larvae, *T. canis* excretory-secretory (TES) antigens and the combination of TES-30 and somatic larvae lysate for detection of *Toxocara* binding antibodies in samples of control patients suffering from *Echinococcus, Strongyloides* or, *Ascaris* infections. Statistically significant positive detection results are shown in bold. Vague results are underlined.

FIG. 4 shows the summary of the ELISA experiments. (a) Sensitivity derived from the results of ELISAs tested with samples of patients suffering from a *Toxocara* infection. (b) Specificity derived from the results of ELISAs tested with samples of the healthy control group. (c) Specificity (parasitosis) derived from the results of ELISAs tested with samples of patients suffering from *Echinococcus, Strongyloides* or *Ascaris* infections. (d) The combined score including the results of (a), (b) and (c).

DETAILED DESCRIPTION OF THE INVENTION

The present inventors surprisingly found that the combined use of a peptide comprising the amino acid set forth in SEQ ID NO:1 and a somatic lysate of *Toxocara canis* larvae results in an immunological assay (for example an ELISA) that provides a well-balanced ratio of high sensitivity and high specificity. This well-balanced ratio of high sensitivity and high specificity can be observed preferably when the peptide and lysate are mixed and co-localized on a diagnostic carrier.

Thus, in a first aspect the present invention is directed to a diagnostically useful carrier comprising (a) a peptide comprising the amino acid sequence set forth in SEQ ID NO:1 or a variant thereof, and (b) a somatic lysate of *Toxocara canis* larvae.

In additional preferred embodiments, the carrier is selected from the group comprising a glass slide, a biochip, a microtiter plate, a lateral flow device, a test strip, a membrane, a line blot, a chromatography column and a bead.

In a second aspect, the present invention relates to a kit comprising the diagnostically useful carrier of the invention and a labeled antibody for detecting a human, Canidae or Rodentia antibody.

In a third aspect, the present invention is directed to a method for diagnosing a *Toxocara* infection comprising detecting in a sample of a patient the presence of an antibody to SEQ ID NO:1 and/or an antibody to a somatic lysate of *Toxocara canis* larvae.

In a fourth aspect, the present invention relates to a composition comprising (a) a peptide comprising the amino acid sequence set forth in SEQ ID NO:1 or a variant thereof, and (b) a somatic lysate of *Toxocara canis* larvae.

In a fifth aspect, the invention further relates to the composition of the invention or the diagnostically useful carrier of the invention for use in the diagnosis of a *Toxocara* infection.

In a sixth aspect, the invention is directed to a method of determining the presence of an antibody against a *Toxocara canis* protein according to SEQ ID NO:1 and/or an antibody against a protein from a somatic lysate of *Toxocara canis* larvae, comprising (i) contacting a sample isolated from a subject having a *Toxocara* infection with a polypeptide comprising SEQ ID NO:1 and/or a variant thereof and with a somatic lysate of *Toxocara canis* larvae, wherein the polypeptide and/or the lysate binds specifically to antibodies binding to SEQ ID NO:1 or the somatic lysate; and (ii) determining the presence of an antibody against SEQ ID NO:1 and/or an antibody against the somatic lysate.

In a seventh aspect, the invention additionally relates to a use of a *Toxocara canis* protein according to SEQ ID NO:1 and a somatic lysate of *Toxocara canis* larvae for the manufacture of a kit for detecting *Toxocara* infection comprising (a) a peptide comprising the amino acid sequence set forth in SEQ ID NO:1 or a variant thereof, and (b) a somatic lysate of *Toxocara canis* larvae.

In preferred embodiments of various aspects of the invention, the *Toxocara* infection is a *Toxocara canis* infection.

In preferred embodiments of various aspects of the invention, the sample is blood, serum, plasma, CSF, urine or saliva.

In other preferred embodiments of various aspects of the invention, the *Toxocara* infection can be distinguished from an *Echinococcus*, a *Strongyloides* and an *Ascaris* infection.

Moreover, in preferred embodiments of various aspects of the invention the peptide and the lysate are conjointly combined.

In preferred embodiments of various aspects of the invention, the antibody against SEQ ID NO:1 and/or the antibody against the somatic lysate is selected from the group comprising IgG, IgA and IgM class antibodies.

In preferred embodiments of various aspects of the invention, the detection or determination comprises a blot assay, chemiluminescence immunoassay, light scattering immunoassay, radiolabeled immunoassay or immunofluorescence assay.

The present invention is based on the inventors' surprising finding that antibodies to SEQ ID NO:1 and a somatic lysate of Toxocara canis larvae may be used for the sensitive and specific diagnosis of a nematode infection, namely a Toxocara infection. Experimentally it is demonstrated that the combined use of Toxocara canis TES-30 (SEQ ID NO:1) and the somatic lysate of Toxocara canis larvae results in a well-balanced assay with high specificity and sensitivity at the same time. Such assay outperforms assays which use the separate protein, the separate lysate and a standard assay that comprises Toxocara excretory-secretory (TES) antigens.

According to the present invention, the (poly)peptides may be recombinant proteins, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", published by GE Healthcare Life Sciences, and in Burgess, R. R., Deutscher, M. P. (2009): Guide to Protein Purification).

In a preferred embodiment, the polypeptide is Toxocara cans TES-30, which has or comprises SEQ ID NO:1 or A0A1D8MBE4 (Uniprot), more preferably SEQ ID NO:1. As throughout this application, any data base code used refers to the sequence available from said data base on the first priority date relating to said application. In another embodiment, polypeptides may be used, which are comprised in a somatic lysate of Toxocara canis larvae. In another preferred embodiment, the polypeptide according to the present invention and used for the various embodiments of the present invention is an isolated polypeptide, wherein the term "isolated", as used herein, means that the polypeptide has been enriched compared to its state upon production using a biotechnological or synthetic approach and is preferably pure, i.e. at least 10, 20, 30, 40, 50, 60, 70, 80, 90, 95 or 99 percent of the polypeptide in the respective sample consists of said polypeptide as judged by SDS polyacrylamide gel electrophoresis followed by Coomassie blue staining and quantitative determination using a computer-aided densitometer. Alternatively, the term "isolated" may refer to enriched solution comprising a variety of different proteins whereas the solution has been purified or essentially been purified from other molecule types, such as lipids or nucleic acid molecules.

In a preferred embodiment, the term "variant", as used herein, may refer to at least one fragment of the full length sequence referred to, for example SEQ ID NO:1 or SEQ ID NO:2, more preferably SEQ ID NO:1, more specifically one or more amino acid or nucleic acid sequence which is, relative to the full-length sequence, truncated at one or both termini by one or more amino acids. Such a fragment comprises or encodes for a peptide having at least 10, 13, 15, 25, 50, 75, 100, 150, 200 or 230 successive amino acids of the original sequence or a variant thereof. The total length of the variant may be at least 13, 25, 30, 40, 50, 60, 70, 80, 90, 100 or more amino acids.

In another preferred embodiment, the term "variant" relates not only to at least one fragment, but also a polypeptide or a fragment thereof comprising amino acid sequences, preferably a fragment comprising at least 25, more preferably 50, more preferably 100, more preferably 150, more preferably 200, more preferably 230 successive amino acids, that are at least 40, 50, 60, 70, 75, 80, 85, 90, 92, 94, 95, 96, 97, 98 99, 99.4, 99.5, 99.6, 99.7, 99.8 or 99.9% identical to the reference amino acid sequence referred to or the fragment thereof, wherein amino acids other than those essential for the biological activity, for example the ability to bind specifically to an antibody of interest, or the fold or structure of the polypeptide are deleted or substituted and/or one or more such essential amino acids are replaced in a conservative manner and/or amino acids are added or deleted such that the biological activity of the polypeptide is at least partially preserved. Known methods comprise various methods that may be used to align two given nucleic acid or amino acid sequences and to calculate the degree of identity, see for example Arthur Lesk (2008), Introduction to bioinformatics, Oxford University Press, 2008, 3$^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007): Clustal W and Clustal X version 2.0. Bioinformatics, 23, 2947-2948) is used applying default settings.

In preferred embodiments, the variant is a polypeptide comprising a sequence that has at least 70%, at least 80%, at least 85%, at least 90% or at least 95% sequence identity to the sequence according to SEQ ID NO:1. In a more preferred embodiment, the variant is a polypeptide comprising a sequence that has at least 80% sequence identity to the sequence according to SEQ ID NO:1.

The structures of proteins related to TES-30/SEQ ID NO:1, specifically the ones of other lectin proteins, are well-known to the skilled person. Such protein structures can be found, for example, under modbase.compbio.ucsf.edu/modbase-cgi/model_details.cgi?query-file=1592383498_9335&
searchmode=default&displaymode=mod
detail&referer=yes&snpflag=&.

Moreover, the skilled person is aware of fragments of TES-30 that provide immunogenic activity. Ebrahimi et al. (Ebrahimi, M. et al. (2019), Int J Pept Res Ther (2019). doi.org/10.1007/s10989-019-09940-1) describe that the TES-30 fragments of amino acid residues 52 to 102 and 172 to 207 have high immunogenicity. Thus in preferred embodiments of the invention the variants of SEQ ID NO:1 comprise the sequence of fragments 52 to 102 (according to SEQ ID NO:3) and/or 172 to 207 (according to SEQ ID NO:4) of TES-30. In even more preferred embodiments, the variants of SEQ ID NO:1 comprise both of SEQ ID NO:3 and SEQ ID NO:4.

In a preferred embodiment, variants may, in addition, comprise chemical modifications, for example isotopic labels or covalent modifications such as glycosylation, phosphorylation, acetylation, decarboxylation, citrullination, hydroxylation and the like. The person skilled in the art is familiar with methods for the modification of polypeptides. Moreover, variants may also be generated by way of fusion with other known polypeptides or other variants.

The variant of the polypeptide has biological activity. In a preferred embodiment, such biological activity is the ability to bind to, preferably capture specifically the respective antibody if the variant is a variant of a sequence from the group comprising SEQ ID NO:1, or SEQ ID NO:2, preferably SEQ ID NO:1. For example, a variant of SEQ ID NO:1 has the ability to capture specifically an antibody to SEQ ID NO:1 in a sample obtained from a subject suffering from or suspected of suffering from a nematode infection, preferably a *Toxocara canis* infection. Such variants have at least one epitope recognized by the antibody to be captured, for example one epitope in SEQ ID NO:1 if an antibody to SEQ ID NO:1 is captured. A variant of SEQ ID NO:2 has the ability to capture specifically an antibody to SEQ ID NO:2 in a sample from a subject suffering from or suspected of suffering from a nematode infection, preferably a *Toxocara canis* infection.

The person skilled in the art is capable of designing variants by starting from the original SEQ ID NO:1 sequence, introducing modifications such as point mutations, truncations and the like and subsequently confirming that the variant still has biological activity by testing whether said variant binds to an antibody to SEQ ID NO:1 in a sample obtained from a subject suffering from the disease to be diagnosed, preferably an infection, more preferably a nematode infection, more preferably a *Toxocara* infection, most preferably a *Toxocara canis* infection. Variants may be identified by identifying naturally occurring fragments derived from the full-length protein or a precursor thereof, for example by purifying them using a polypeptide comprising SEQ ID NO:1 or SEQ ID NO:2, preferably SEQ ID NO:1, as an affinity ligand followed by N-terminal Edman sequencing and/or tryptic digest in combination with mass spectrometry, and using them to practice the invention. Conservative amino acid substitutions may be used for all variants.

Within the scope of the present invention is a diagnostically useful carrier comprising a means for specifically capturing an antibody to an antigen such as SEQ ID NO:1 or SEQ ID NO:2, preferably SEQ ID NO:1 and the somatic lysate of *Toxocara canis* larvae. In a preferred embodiment, the term "specifically capturing an antibody", as used herein, refers to the ability to bind specifically to the antibody of interest, preferably an IgA, IgM or IgG class antibody, to the effect that it is bound and may be removed from the sample, whereas other antibodies, preferably from the same class and/or to another antigen, are essentially not bound and remain in the sample. The antibody is preferably an antibody that binds to the antigen of interest only such as the one represented by SEQ ID NO:1 or SEQ ID NO:2, preferably SEQ ID NO:1 and the somatic lysate of *Toxocara canis* larvae.

The diagnostically useful carrier according to the invention serves as a scaffold for the one or more means for specifically capturing an antibody, preferably a diagnostically relevant antibody to a *Toxocara* antigen such as the one represented by SEQ ID NO:1 and/or the somatic lysate of *Toxocara canis* larvae. Said carrier is suitable for carrying out a diagnostic method. By using a carrier rather than free, soluble means for specifically capturing an antibody, it is more straightforward to isolate and separate from the sample a complex comprising the means and the antibody and to wash said complex, for example for the purpose of removing any molecules binding non-specifically to the means, complex or carrier. In a preferred embodiment, the diagnostically useful carrier is a diagnostic device, preferably selected from the group comprising a bead, preferably a paramagnetic bead, a test strip, a microtiter plate, a microarray, a blot and a membrane, and is preferably a line blot or microtiter plate, more preferably a microtiter plate. The carrier may comprise one or more controls, preferably all from the group comprising an IgM conjugate control, which confirms that a secondary antibody recognizing human IgM has been added, an IgG conjugate control, which confirms that a secondary antibody recognizing human IgG has been added, an IgA conjugate control, which confirms that a secondary antibody recognizing human IgA has been added, a serum control, which confirms that serum has been added, a negative control, which shows that there is no false positive signal, a positive control, which shows that there is no false negative signal, and one or more calibrator controls, which are preferably weak positive spots that allow for a semi-quantitative determination. If the carrier comprises several antigens, the carrier may comprise a separation band, which may indicate the spatial separation of bands, for example the control bands on one hand and the antigen bands on the other. Moreover, the carrier may comprise a cut-off band.

The diagnostically useful carrier may be a slide, preferably glass or plastic slide for microscopy, comprising one or more eukaryotic cells, each spatially separated from each other and each expressing a polypeptide that is a means for specifically capturing an antibody. The one or more eukaryotic cells may be live cells, but are preferably fixed cells. State of the art protocols are available for fixing cells, for example using methanol or formaldehyde. Indirect immunofluorescence may be used to detect an antibody captured using such a carrier. One cell may comprise the peptide according to SEQ ID NO:1 or a variant thereof. In addition, a *Toxocara canis* larvae lysate can be immobilized on the slide.

The diagnostically useful carrier may be a bead configured for an immunoassay comprising a polypeptide comprising SEQ ID NO:1 or a variant thereof and the somatic lysate of *Toxocara canis* larvae. In a more preferred embodiment, the bead is a solid bead comprising carbohydrate such as sepharose or synthetic polymer such as latex, preferably a paramagnetic bead, which may be removed from a solution and concentrated, preferably at the surface of a vessel, by applying a magnetic field. The bead comprises a means for capturing an antibody linked to the bead by a covalent or non-covalent bond. A mixture of beads, for example one of which linked to SEQ ID NO:1 or a variant thereof, and/or one linked to SEQ ID NO:2 or a variant thereof, may be used.

In a preferred embodiment, the diagnostically useful device is a microtiter plate comprising a range of wells configured for an immunoassay such as an ELSA assay. Preferably the microtiter plate comprises a well coated with a means for specifically capturing an antibody to SEQ ID NO:1 and or SEQ ID NO:2, preferably SEQ ID NO:1 and the somatic lysate of *Toxocara canis* larvae, which means is preferably a polypeptide comprising SEQ ID NO:1 or a variant thereof and the somatic lysate of *Toxocara canis* larvae. In a preferred embodiment, the term "microtiter plate" is a diagnostic device, preferably made from glass or plastic, more preferably plastic, comprising one or more, preferably more than one, more preferably at least 8 wells, in which reactions in liquid buffer may be run separately without cross-contamination. At least one of the wells is coated with a polypeptide, preferably an antigenic polypeptide that may be used to specifically capture a diagnostically useful antibody. If more than one means for specifically detecting an antigen is used, then preferably each means is in a well separate from other means. The microtiter plate may be used for running several samples in parallel, preferably in an automated fashion. The wells are preferably compatible with at least one routine detection techniques such colorimetry, immunofluorescence, detection of enzymatic activity, chemiluminescence, radioactivity or the like. In addition, a separate well may include one or more antigens for detecting another nematode infection.

In preferred embodiments of the present invention, the methods and assays do not comprise a step of nucleic acid amplification, such as PCR or loop-mediated isothermal amplification (LAMP).

In a preferred embodiment, the term "specifically detecting a captured antibody", as used herein, means that the antibody binding specifically to the means for specifically capturing the antibody, preferably a polypeptide comprising SEQ ID NO:1 or SED ID NO:2, preferably SEQ ID NO:1 or a variant thereof or a somatic lysate of *Toxocara canis* larvae, following capture, binds specifically to the means for detecting the antibody, for example a secondary antibody. In a preferred embodiment, the term "specifically capturing an antibody", as used herein, means that the means for specifically capturing an antibody binds specifically to the antibody and does not bind, at a significant or detectable level to any other antibody. In a preferred embodiment, the term "binding specifically", as used herein, means that the binding is stronger than a binding reaction characterized by a dissociation constant of $1\times10^{-5}$ M, more preferably $1\times10^{-7}$ M more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7.

In a preferred embodiment, the term "specifically detecting of an antibody", which antibody belongs to a certain class of antibodies, for example IgA, IgM or IgG class antibodies, means that said antibody is detected in an assay spatially separated from any binding reaction involving the detection of antibodies to the same antigen associated with another class and, more preferably, no antibody from another class against the same antigen is detected in the same reaction, for example an ELISA well. In other words, the assay is carried out such that the readout allows to distinguish between antibody classes, for example IgG or IgM antibodies from other antibody classes, and to conclude and detect specifically to which antibody class the detected antibody belongs or to detect only a specific class of antibody to an antigen of interest, preferably IgM antibodies to SEQ ID NO:1 or the somatic lysate of *Toxocara canis* larvae or IgG antibodies to SEQ ID NO:1 or the somatic lysate of *Toxocara canis* larvae. This does not rule out that antibodies to the same antigen, but associated with another class of antibodies, may be detected in a spatially separate reaction simultaneously. For example, binding reactions involving the same antigen such as SEQ ID NO:1 or SEQ ID NO:2 or a variant thereof, may be run in separate wells of an ELISA microtiter plate, but may be developed using secondary antibodies binding to different classes of antibodies, for example IgM and IgG, respectively.

In a preferred embodiment, an IgG class antibody to a peptide comprising SEQ ID NO:1 and/or a somatic lysate of *Toxocara canis* larvae is detected.

According to the present invention, a means for specifically detecting a captured antibody is provided or used to practice the present invention, optionally as part of a kit. In a preferred embodiment, the term "a means for specifically detecting a captured antibody", as used herein, refers to a reagent that binds specifically to the captured antibody, preferably to its constant region, such that the antibody captured or to be captured remains capable of binding to its antigen. The sequence of the constant region depends on the organism from which the sample is taken and analyzed, and the antibody class. Preferably, the means binds to human IgA IgM or IgG class antibodies. If an antibody to SEQ ID NO:1 is detected, it is preferred that the secondary antibody recognizes the constant region of IgG class antibodies. If an antibody to the somatic lysate of *Toxocara canis* larvae is detected, it is preferred that the secondary antibody recognizes constant region of IgG class antibodies.

In a more preferred embodiment, the means for specifically detecting a captured antibody is selected from the group comprising a secondary antibody, an aptamer and an anticalin (Skerra, A. (2008). "Alternative binding proteins: anticalins—harnessing the structural plasticity of the lipocalin ligand pocket to engineer novel binding activities". FEBS J. 275 (11): 2677-83) and is most preferably a secondary antibody. A secondary antibody may be a mammalian antibody, more preferably selected from the group comprising a cow, goat, chicken, rat, murine, porcine, equine or rabbit antibody. The means may comprise a detectable label, preferably from the group comprising an enzymatically active, colored label, preferably from the group comprising a gold and a latex label, chemiluminescent and fluorescent label.

If a polypeptide is used as the means for specifically capturing an antibody, said polypeptide, preferably comprising one or more sequences selected from the group comprising SEQ ID NO:1 and/or a somatic lysate of *Toxocara canis* larvae, when used to carry out the teachings of the present invention, may be provided in any form and at any degree of purification, from tissues or cells comprising said polypeptide in an endogenous form, more preferably cells overexpressing the polypeptide, crude or enriched lysates of such cells, to purified and/or isolated polypeptide which may be essentially pure. In a preferred embodiment, the term "overexpressing", as used herein, means that the cell, preferably a eukaryotic, more preferably a mammalian or insect, more preferably a mammalian, more preferably a human cell, most preferably a HEK293 or HEK293T cell, has been genetically engineered such that it expresses more of the protein of interest than a non-engineered wild type cell would. In a preferred embodiment, the polypeptide is a native polypeptide, wherein the term "native polypeptide", as used herein, refers to a folded polypeptide comprising at least 15, 30, 50, 100 150, 200, 300 or 350 amino acids, preferably more than 30 amino acids, more preferably to a folded polypeptide purified from tissues or cells, more preferably from mammalian cells or tissues, optionally from non-recombinant tissues or cell. In another preferred embodiment, the polypeptide is a linear peptide having at least 7, more preferably at least 10 amino acid residues. If a native polypeptide is used, it is preferably enriched compared to its natural state. A recombinant polypeptide may comprise a C-terminal or N-terminal tag for affinity purification, immobilization or detection such as a His tag, as exemplified by SEQ ID NO:2, or a streptavidin tag, preferably a streptavidin, which tag may preferably be removed by cleavage using a protease recognizing a protease cleavage site in a polypeptide linker between the tag and the N terminus or C-terminus, respectively, as part of the purification or method. The cleaved polypeptide may subsequently be attached to a diagnostically useful carrier to yield the diagnostically useful carrier according to the present invention. In another preferred embodiment, the means for specifically capturing an antibody is a *Toxocara* infected eukaryotic, preferably human cell. Such a cell may be evaluated by fluorescence microscopy. The cells may be transiently or stably transfected, preferably transiently transfected, preferably with a vector comprising a sequence encoding SEQ ID NO:1 or SEQ ID NO:2, preferably SEQ ID NO:1, under the control of an inducible or constantly induced promotor.

Said means for specifically capturing an antibody, together with the insoluble carrier to which it is attached, may be separated from a sample from a subject in a straightforward manner, for example by filtration, centrifugation, magnetism or decanting. Said means may be immobilized in a reversible or irreversible manner. For example, the immobilization is reversible if the means interacts with the carrier via ionic interactions which may be masked by addition of a high concentration of salt or if the molecule is bound via a cleavable covalent bond or a non-covalent bond. By contrast, the immobilization is irreversible if the means is tethered to the carrier via a covalent bond that cannot be cleaved in aqueous solution. The means may be indirectly immobilized, for example by immobilizing an antibody or other entity having affinity to the polypeptide, followed by addition of the means and formation of a means-antibody complex. A non-covalent bond may be made by chemically attaching a ligand to the carrier, preferably via a covalent bond, and fusing to the means a polypeptide having affinity to the ligand. In a preferred embodiment, the ligand is selected from the group comprising biotin, in which case the polypeptide having affinity may be streptavidin or a variant thereof binding to biotin, glutathione (polypeptide having affinity: glutathione-S-transferase), Nickel (polypeptide having affinity: His tag), Flag tag (polypeptide having affinity: anti-flag antibody), carbohydrate such as maltose or cellulose (polypeptide having affinity: maltose or cellulose binding protein), and is preferably biotin.

According to the present invention, a nucleic acid encoding the polypeptide according to the present invention such as a polypeptide comprising SEQ ID NO:1 or SEQ ID NO:2, preferably SEQ ID NO:1 or a variant thereof, optionally with an inducible promotor, which polypeptide is preferably for use for the diagnosis of a disease or the manufacture of a kit or reagent for such use, is provided. Said nucleic acid may be a part of a vector, preferably for expressing said nucleic acid. A eukaryotic or prokaryotic, preferably eukaryotic cell comprising this vector and preferably expressing the polypeptide encoding by the vector, is also provided. The nucleic acid, the vector and the cell may be used for the manufacture of a kit for use according to the present invention such as use of an antibody to SEQ ID NO:1 or SEQ ID NO:2, preferably SEQ ID NO:1. The nucleic acid may be expressed, the polypeptide encoded purified and used, preferably immobilized on a diagnostically useful carrier, in order to make the diagnostically useful carrier according to the present invention. The nucleic acid may be used to design and prepare a nucleic acid construct encoding a variant of the polypeptide for expression and use of the resulting variant for the preparation of a diagnostically useful carrier and for the detection of the respective antibody such as an antibody to SEQ ID NO:1 or SEQ ID NO:2, preferably SEQ ID NO:1.

The inventive teachings provide a kit, preferably for diagnosing an infection, more preferably for diagnosing a nematode infection, most preferably a *Toxocara* infection. Such a kit is a container that comprises specific reagents required to practice the inventive method, in particular the diagnostically useful carrier according to the present invention, optionally in addition to one or more reagents and solutions required to practice the inventive method, preferably selected from or all from the group comprising sample dilution buffer, washing buffer and a means for detecting any specifically captured antibody and optionally a means for detecting the specifically captured antibody, which may optionally be attached to the secondary antibody, for example a fluorescent, enzymatically active, radioactive, chemiluminescent, preferably electrochemiluminescent label or a spin label. The kit may comprise a chemical solution for carrying out a detection reaction such as 3,3', 5,5'-tetramethylbenzidine, p-Nitrophenyl Phosphate, 2,2'-Azinobis [3-ethylbenzothiazoline-6-sulfonic acid or o-phenylenediamine dihydrochloride for a colorimetric reaction tripropylamine for an electrochemiluminescence reaction. Furthermore, it may comprise instructions detailing how to use the kit and the inventive diagnostically useful carrier for contacting the inventive polypeptide with a bodily fluid sample from a subject, preferably a human subject. The kit may comprise a negative and/or a positive control serum, more preferably both.

Furthermore, the kit may comprise a positive control, for example a recombinant antibody known to bind to SEQ ID NO:1 and/or a recombinant antibody known to bind to the somatic lysate of *Toxocara canis* larvae, and a negative control, for example a protein having no detectable affinity to SEQ ID NO:1 or to the somatic lysate of *Toxocara canis* larvae. Finally, the kit may comprise one or more calibrators, which is preferably a solution comprising a SEQ ID NO:1-binding and/or a somatic lysate of *Toxocara canis* larvae binding, preferably SEQ ID NO:1-binding antibody for preparing a calibration curve. In a more preferred embodiment, the kit comprises more than one, preferably three or more calibrators comprising different concentrations of an antibody to SEQ ID NO:1, which antibody is preferably recognized by a secondary antibody to human IgG class antibodies. In a more preferred embodiment, the kit comprises at least one antibody to the somatic lysate of *Toxocara canis* larvae, which antibody is preferably recognized by a secondary antibody to human IgG class antibodies. Such calibrator may be or comprise a chimeric antibody comprising a human constant region and optionally a variable region from a mammal other than a human. If more than one calibrator is used, the two or more calibrators comprise different concentrations of the antibody, preferably at a range of concentrations that allow the user to set up a calibration curve.

If IgM class antibodies binding to SEQ ID NO:1 or the somatic lysate of *Toxocara canis* larvae, preferably SEQ ID NO:1 are detected, IgM and IgA class antibodies may be removed or their concentration may be decreased prior to determining the IgG class antibodies. This may be achieved by pre-absorbing IgM and IgA class antibodies, for example by contacting them with an anti-IgM or anti-IgA antibody, for example a mammalian, preferably goat anti-human IgM or IgA antibody. This antibody may absorb the antibodies that may interfere with the IgG detection assay. Suitable reagents are commercially available, for example EUROSORB commercialized by EUROIMMUN, Lübeck. Alternatively, this may be achieved by isolating the entirety of IgG class antibody prior to detecting an IgG antibody to SEQ ID NO:1 or SEQ ID NO:2, preferably SEQ ID NO:1.

For therapeutic purposes, a vaccine may be provided that comprises the polypeptide comprising SEQ ID NO:1 and/or the somatic lysate of *Toxocara canis* larvae or variants thereof that may be formulated with one or more diluents, one or more glidants, and/or one or more filling agents. The preparation of suitable formulations is described in the state of the art, for example in US20130022631A1. The vaccine formulation may comprise, in addition to the purified polypeptide, a pharmaceutically accepted buffer such as phosphate or phosphate-citrate buffer in the pH range 6.4-7.5 with added stabilizing agents that may include one or more of the following, but is not limited to: human serum albumin, gelatin, reducing and non-reducing sugars, amino acids, polyols such as sorbitol and mannitol, glycerol organic and inorganic salts, polyvinyl pyrrolidone etc. The stable formulation may be in a liquid form is suitable for intramuscular/intradermal/subcutaneous/intravenous administration in a human host. The stable formulation may be in a dry lyophilized form can be reconstituted with a suitable solvent before administration. The formulations may be suitable for oral and intranasal administration in humans.

The invention provides a pharmaceutical composition or a vaccine, which composition or immunogenic composition such as a vaccine comprises a polypeptide comprising SEQ ID NO:1 and/or the somatic lysate of *Toxocara canis* larvae or variants thereof. An immunogenic composition or vaccine may comprise components to inactivate a nematode or bacteria and stabilize the vaccine, helping to preserve the vaccine and prevent it from losing its potency over time. Adjuvants are added to vaccines to simulate the production of antibodies against the vaccine to make it more effective. An adjuvant could be organic or inorganic. The most common inorganic adjuvants for human vaccines include aluminum phosphate and aluminum hydroxide. Organic adjuvants could be based on the organic compound squalene and an oil [squalene] in water adjuvant can be used.

An immunogenic composition may comprise stabilizers that help the vaccine to maintain its effectiveness during storage, e.g., $MgCl_2$, $MgSO_4$, lactose-sorbitol, or sorbitol-gelatin, and preservatives to prevent bacterial and fungal growth, e.g., thiomersal, formaldehyde, or phenol derivatives, antibiotics. The composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the inventive polypeptide to a subject.

The inventive method for diagnosing a nematode infection, preferably for distinguishing a *Toxocara* infection from an *Echinococcus*, a *Strongyloides* and an *Ascaris* infection, may comprise the step detecting in a first sample from a subject an IgG class antibody to SEQ ID NO:1 and a of a somatic lysate of *Toxocara canis* larvae, optionally further comprising detecting in said first sample an IgM and/or IgA class antibodies to SEQ ID NO:1 and a of a somatic lysate of *Toxocara canis* larvae.

The inventive method, kit and carriers may be used to detect a nematode infection. In a preferred embodiment, the term "nematode infection", as used herein, refers to an infection of a person who suffers from a *Toxocara* infection, more preferably a *Toxocara canis* infection.

In preferred embodiments, the terms "detecting in a sample" and/or "determining in a sample", as used herein, refer to the qualitative or quantitative measurement of a compound or molecule in said sample. In many cases detecting or detecting the presence of an antibody, optionally meaning determining whether the concentration of the antibody is beyond a certain threshold preferably as set by measurement using ELISA, preferably as described in the examples, in the implicit detection limit by this method, often suggested by the detection limit, in the sample, is sufficient for the diagnosis. If the antibody can be detected, this will be information instrumental for the clinician's diagnosis and indicates an increased likelihood that the patient suffers from a disease. In a preferred embodiment, the relative concentration of the antibody in the serum, compared to the level that may be found in the average healthy subject, may be determined. In a preferred embodiment, the term "detecting the presence", as used herein, means that it is sufficient to check whether a signal sufficiently beyond any background level may be detected using a suitable complex detection method that indicates that the antibody of interest is present or more antibody of interest is present than would be in a healthy subject. In a more preferred embodiment this may involve determining whether the concentration is at least 0.1, preferably 0.2, 0.5, 1, 2, 5, 10, 20, 25, 50, 100, 200, 500, 1000, 10000 or 100000 times higher than the concentration of the antibody of interest found in the average healthy subject.

In a preferred embodiment, the term "diagnosis", as used herein, refers to any kind of procedure aiming to obtain information instrumental in the assessment whether a patient suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of a patient with regard to a certain treatment, for example the administration of suitable drugs such as drugs for the desensitization of allergic patients. In other words, the term "diagnosis" comprises not only diagnosing, but also prognosticating and/or monitoring the course of a disease or disorder.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i.e. a systematic diagnostic procedure considering the likelihood of a range of possible conditions on the basis of a range of diagnostic parameters. The term "diagnosis" may also refer to a method or agent used to choose the most promising treatment regime for a patient. In other words, the method or agent may relate to selecting a treatment regimen for a subject.

The invention may be used to provide a diagnosis or a prognosis whether a subject suffers from visceral larva migrans (VLM), ocular larva migrans (OLM), Weingarten's disease, Frimodt-Møller's syndrome or eosinophilic pseudoleukemia, nematode ophthalmitis, toxocaral disease, toxocarose or covert toxocariasis.

A "*Toxocara* infection", as used herein, refers to the infection of a subject with *Toxocara canis, Toxocara cati, Toxocara mystax* or *Toxascaris leonine*.

The term "sample", as used herein, refers to a fluid (blood, serum, urine, semen, CSF), intact cells or extracts thereof, or tissue samples. The sample may be a clinical cytology specimen (e.g., fine needle breast biopsy or pulmonary cytology specimen) or a human tissue specimen from, for example, stomach, lung, breast, ovarian, pancreatic, prostate or brain tumors. The tissue specimen may be fresh or frozen. Preferably, the sample is whole blood or serum.

"Subject" or "patient", as interchangeably used herein, relate to a human or an animal, preferably a mammal, more preferably to a human. Canidae, Rotendia or Felidae and most preferably a human.

The present invention relates to a method comprising the step detecting in a sample from a subject the presence or absence of an antibody to an antigenic polypeptide such as a polypeptide comprising a SEQ ID NO:1 and a somatic lysate of *Toxocara canis* larvae. This method preferably comprises immobilizing said antibody followed by specific detection of said antibody, for example by way of the steps a) (optionally) providing a sample from a subject, b) contacting the sample with the diagnostically useful carrier according to the present invention under conditions compatible with the formation of a complex comprising the diagnostically useful carrier and the antibody, more specifically the means for specifically capturing the antibody and the antibody, c) isolating any said complex, for example by removing the sample, d) optionally washing said complex, and e) optionally detecting said complex. The method is preferably an in vitro method. The detection of the complex for the prognosis, diagnosis, methods or test kit according to the present invention comprises the use of a method selected from the group comprising immunodiffusion techniques, immunoelectrophoretic techniques, light scattering immunoassays, agglutination techniques, labeled immunoassays such as those from the group comprising radiolabeled immunoassay, enzyme immunoassays such as colorimetric assays, chemiluminescence, preferably electrochemiluminescence, immunoassays and immunofluorescence techniques. The person skilled in the art is familiar with these methods, which are also described in the state of the art, for example in Zane, H. D. (2001): Immunology—Theoretical & Practical Concepts in Laboratory Medicine. W. B. Saunders Company, in particular in Chapter 14. The method may further involve testing the avidity of antibodies to SEQ ID NO:1 or the somatic lysate of *Toxocara canis* larvae in the sample, preferably of antibodies to SEQ ID NO:1.

In preferred embodiments, the *Toxocara canis* larvae is in larval stage L2. *Toxocara canis* larvae can be cultivated and obtained according to de Savigny [de Savigny (1975), J. Parasitol., 61 (1975), pp. 781-782]. Briefly, the female worms are collected from puppies after deworming with piperazine, an anthelmintic drug that does not kill eggs, or after necropsy. Female worms are washed with tap water and then dissected. The genital tracts undergo a controlled artificial digestion in a pepsin-HCl mixture to remove the surrounding tissues. The collected eggs are distributed in glass tubes that are plugged with cotton wool and contain a 0.9% NaCl solution supplemented with 1% formalin. The tubes are incubated at 37° C. in a stirring water bath for 2-3 weeks. Periodically, the embryonation level is assessed by microscopic inspection. When the rate is approximately 50%, the eggs are dissected in a Potters grinder. Further steps require a sterile environment provided by a laminar flow bench. The resulting mixture, which contains living and dead larvae along with eggshell fragments, is diluted in RPMI 1640 medium. Viable larvae are extracted from the crude mixture using a method similar to the Baermann technique employed to retrieve *Strongyloides stercoralis* larvae from stools. The larvae are then distributed in flat vials of the type used in virology for cell cultures that are filled with RPMI 1640 medium supplemented with glutamine. The final larval concentration is approximately 1000 larvae/mL. The vials are incubated at 37° C. in a 5% $CO_2$ atmosphere. The terms "somatic lysate", "lysate" and "extract", as interchangeably used herein, refer to an aqueous solution or suspension comprising the cellular proteins and factors produced by lysis of *Toxocara canis* larvae. Such a lysate may comprise macromolecules, like DNA, RNA, proteins, peptides, carbohydrates, lipids and the like and/or micromolecules, like amino acids, sugars, lipid acids and the like, or fractions from the lysed cells. The cellular fragments present in such a lysate may be of smooth or granular structure. Preferably, said aqueous medium is water, physiological saline, or a buffer solution.

The term lysate, as used herein, also encompasses preparations or fractions prepared or obtained from the above-mentioned lysates. These fractions can be obtained by methods known to those skilled in the art, e.g., chromatography, including, e.g., affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or other protein chemical, molecular biological, biochemical, immunological, chemical or physical methods to separate above components of the lysates. In a preferred embodiment those fractions which are more immunogenic than others are preferred. Those skilled in the art are able to choose a suitable method and determine its immunogenic potential by referring to the above general explanations and specific explanations in the examples herein, and appropriately modifying or altering those methods, if necessary.

The term "conjointly combined", as used herein, refers to a diagnostically useful carrier that comprises at least two antigens, namely a peptide comprising a sequence set forth in SEQ ID NO:1 or variant thereof and a somatic lysate of *Toxocara canis* larvae. In preferred embodiments, the antigens are located on the diagnostically useful carrier such that both antigens can be contacted with the identical sample at the same time. In even more preferred embodiments, the peptide comprising a sequence set forth in SEQ ID NO:1 or variant thereof and the somatic lysate of *Toxocara canis* larvae are mixed before they are attached to the diagnostically useful carrier of the invention. This means that if the diagnostically useful carrier is a microtiter plate for carrying out ELISA, the peptide comprising a sequence set forth in SEQ ID NO:1 and the antigens comprised in the somatic lysate of *Toxocara canis* larvae may be co-localized in the same well. If the diagnostically useful carrier is a membrane, both antigens may be co-localized to form one protein spot, dot or lane.

In preferred embodiments, the antigens, namely the peptide comprising a sequence set forth in SEQ ID NO:1 or variant thereof and the somatic lysate of *Toxocara canis* larvae, are in a solution before being attached to the diagnostically useful carrier, whereas said solution has an antigen concentration of not more than 40.0 µg/ml, not more than 35.0 µg/ml, not more than 30.0 µg/ml, not more than 25.0 µg/ml, not more than 20.0 µg/ml, not more than 18.0 µg/ml, not more than 16.0 µg/ml, not more than 14.0 µg/ml, not more than 12.0 µg/ml, not more than 10.0 µg/ml, not more than 8.0 µg/ml, not more than 7.5 µg/ml, not more than 7.0 µg/ml, not more than 6.5 µg/ml, not more than 6.0 µg/ml, not more than 55 μg/mL not more than 5.0 μg/ml, not more than 4.5 μg/ml, not more than 4.0 μg/ml, not more than 3.5 μg/ml, not more than 3.0 μg/ml, not more than 2.5 μg/ml or not more than 2.0 μg/ml comprising one or both antigens. In other preferred embodiments, the antigen (namely the peptide comprising a sequence set forth in SEQ ID NO:1 or variant thereof and the somatic lysate of *Toxocara canis* larvae) density for one or both antigens on the surface of the diagnostically useful carrier is not more than 2.0 μg, not more than 1.8 μg, not more than 1.6 μg, not more than 1.4 μg, not more than 1.2 μg, not more than 1.0 μg, not more than 0.9 μg, not more than 0.8 μg, not more than 0.7 μg, not more than 0.6 μg, not more than 0.5 μg, not more than 0.4 μg, not more than 0.3 μg, not more than 0.2 μg, not more than 0.1 μg or not more than 0.05 μg per 0.32 cm$^2$ which corresponds to the area of a single well of a 96-well plate. For other diagnostically useful carriers, such as slides and blot membranes, identical antigen densities can be used in preferred embodiments.

The present invention is further illustrated by the following examples, sequences and figures from which further features, embodiments, aspects and advantages of the present invention may be taken. All methods and materials similar or equivalent to those described herein can be used in the practice or testing of the present invention, with suitable methods and materials being described herein. All publications, patent applications, patents, and other references mentioned herein are incorporated by reference in their entirety. Further, the materials, methods, and examples are illustrative only and are not intended to be limiting, unless otherwise specified.

```
(Toxocara canis TES-30)
                                    SEQ ID NO: 1
MIAAIVAILLCLHLSATNACATNNDCWQVCVNNVCVANNQGCNPPCVAPQ

VCVAPMCVAPPAATTTAAPGVTTTRPRACPPNWTPFNNNCYIASLPGRFL

FNQASDWCTQTGSRVVWFDQSTVGNFGSELNFVNSFAVGRGVTRYWIGVN

RQFGQWVFTNGSPVIFSNWRPSQPDGCCGSNVTCAFVNYANFLGQWDDAP

CGSLFTTPQGFVCKRPL (Toxocara canis TES-30 N-terminal His-Tagged)
                                    SEQ ID NO: 2
MSHHHHHHHHSMIAAIVVLLCLHLSATNACATNNDCGIFQVCVNNVCVAN

NQGCNPPCNAPQVCVAPMCVAPPPAATTTAAPGVTTTRPRACPPNWTPFN

NNCYIASLPGRFLFNQASDWCTQMSRVVWFDQSTVGNFGSELNFVNSFAV

GRGVTRYWIGVNRQFGQWVFTNGSPVIFSNWRPSQPDGCCGSNVTCAFVN

YANFLGQWDDAPCGSLFTTPQGPVCKRPL (Toxocara canis TES-30 fragment 52 to 102 aa)
                                    SEQ ID NO: 3
VCVAPMCVAPPPAATTTAAPGVTTTRPRACPPNWTPFNNNCYIASLPGRF

L (Tavocara canis TES-30 fragment 172 to 207 aa)
                                    SEQ ID NO: 4
RPSQPDGCCGSVTCAFVNYANFLGQWDDAPCGSLF
```

FIG. 1 shows results of different ELISAs using *T. canis* TES-30, somatic lysate *T. canis* larvae, *T. canis* excretory-secretory (TES) antigens and the combination of TES-30 and somatic larvae lysate for detection of *Toxocara* binding antibodies in samples of patients suffering from a *Toxocara* infection. Statistically significant positive detection results are shown in bold. Vague results are underlined.

FIG. 2 shows results of different ELISAs using *T. canis* TES-30, somatic lysate *T. canis* larvae, *T. canis* excretory-secretory (TES) antigens and the combination of TES-30 and somatic larvae lysate for detection of *Toxocara* binding antibodies in samples of a healthy control group. Statistically significant positive detection results are shown in bold. Vague results are underlined.

FIG. 3 shows results for different ELISAs using *T. canis* TES-30, somatic lysate *T. canis* larvae, *T. canis* excretory-secretory (TES) antigens and the combination of TES-30 and somatic larvae lysate for detection of *Toxocara* binding antibodies in samples of control patients suffering from *Echinococcus, Strongyloides* or *Ascaris* infections. Statistically significant positive detection results are shown in bold. Vague results are underlined.

FIG. 4 shows the summary of the ELISA experiments. (a) Sensitivity derived from the results of ELISAs tested with samples of patients suffering from a *Toxocara* infection. (b) Specificity derived from the results of ELISAs tested with samples of the healthy control group. (c) Specificity (parasitosis) derived from the results of ELISAs tested with samples of patients suffering from *Echinococcus, Strongyloides* or *Ascaris* infections. (d) The combined score including the results of (a), (b) and (c).

EXAMPLES

Following experiments were performed to evaluate different *Toxocara* antigens in an indirect ELISA for the detection of specific anti-*Toxocara* IgG antibodies in human serum or plasma. The following antigens were analyzed for a) sensitivity, b) specificity for *Toxocara* negative patient samples and c) specificity for samples positive for other parasitoses.

Description of Tested *Taxocara* Spp. Antigens

The following antigens were analyzed: 1) recombinant mTES-30 of *Toxocara* spp., 2) somatic antigen of *Toxocara canis* larvae, 3) excretory-secretory (E/S) of *Toxocara canis* larvae and 4) somatic antigen of *T. canis* combined with recombinant mTES-30.

Samples:

Panel 1 (Sensitivity Panel):

The sensitivity panel contains 16 samples of patients with proven *Toxocara* infection. The samples were serologically confirmed via ELISA and/or blot technique (FIG. 1).

Panel 2 (Specificity Panel):

The specificity panel contains 48 samples which originate from healthy individuals (pregnant woman, children and blood donors from Germany) (FIG. 2).

Panel 3 (Specificity Panel):

The specificity panel contains 32 samples of patients with proven infections for ascariasis, echinococcosis and strongyloidiasis. The samples were serologically confirmed via ELISA (FIG. 3).

Experiments:

1. Preparation of Coated Microtiter Plates

The following antigens were used:

Recombinant mTES-30 of *Toxocara* spp.

Somatic antigen of *Toxocara canis* larvae (lysate)

Excretory-secretory (E/S) of *Toxocara canis* larvae

Somatic antigen of *T. canis* (lysate) combined with recombinant mTES-30

For use in microtiter ELISA these antigens were diluted in carbonate buffer to final concentrations of:

Recombinant mTES-30 of *Toxocara* spp. 2.0 μg/ml

Somatic antigen of *Toxocara canis* larvae 0.5 μg/ml

Excretory-secretory (E/S) of *Toxocara canis* larvae 1.0 μg/ml

Somatic antigen of *T. canis* 0.5 μg/ml combined with 2.0 μg/ml recombinant mTES-30

ELISA microtiter plates (NUNC, Roskilde, Denmark) were coated with 100 μl of antigen dilution per well.

2. Experimental Procedure

Sample were diluted 1:101 in IgG sample buffer, were applied to microtiter plates and incubated as described for commercial EUROIMMUN ELISA Test-Kits (e.g. EI 2311-9601 G). In brief: 60 min at 37° C.; 3 washing steps using EUROIMMUN wash buffer: addition of 100 μl of peroxidase-labelled anti-human IgG conjugate (goat) per well; incubation for 30 min at 37° C.; 3 washing steps using EUROIMMUN wash buffer: addition of 100 μl of chromogen/substrate solution (TMB/$H_2O_2$) per well; incubation for 30 min at room temperature; addition of 100 μl stop-solution (0.5 M sulfuric acid); measurement of optical density at 450 nm.

Panel 1 was used for evaluation of sensitivity of the respective antigens for detection of specific anti-*Toxocara* IgG antibodies. Panel 2 and 3 were incubated to determine specificity of the test system.

3. Interpretation of Results

1. Sensitivity of Recombinant mTES-30, Somatic Antigen of *T. canis* Larvae, E/S-Antigen of *T. canis* and the Combination of mTES-30 and the Somatic Larvae Antigen Comparison of recombinant mTES-30 of *Toxocara* spp., somatic antigen of *Toxocara canis* larvae, excretory-secretory (E/S) of *Toxocara canis* larvae and the combination of somatic antigen of *T. canis* with recombinant mTES-30 revealed sensitivities as shown in FIG. 4a.

The sample set used for evaluation of sensitivity of this test are samples originating from patients positive for anti-*Toxocara* IgG antibodies. The combination of recombinant mTES-30 with somatic antigen of *T. canis* larvae suggests being more sensitive for the detection of anti-*Toxocara* IgG antibodies than the single antigens and reveals a comparable sensitivity to the commercially used E/S-antigen of *T. canis*.

2. Specificity of Recombinant mTES-30, Somatic Antigen of *T. canis* Larvae, E/S-Antigen of *T. canis* and the Combination of mTES-30 and the Somatic Larvae Antigen Comparison of recombinant mTES-30, somatic antigen of *T. canis* larvae, E/S-antigen of *T. canis* and the combination of mTES-30 and the somatic larvae antigen reveals specificity as shown in FIG. 4b.

Measured anti-IgG antibodies may result from earlier *Toxocara* contact (prevalence in Germany 2-5%). The recombinant mTES-30 as well as the somatic antigen of *T. canis* larvae reveals high specificity. In this study the specificity of the E/S-antigen of *T. canis* results in lowest specificity.

3. Specificity Against Other Parasitoses of Recombinant mTES-30, Somatic Antigen of *T. canis* Larvae, E/S-Antigen of *T. canis* and the Combination of mTES-30 and the Somatic Larvae Antigen Comparison of recombinant mTES-30, somatic antigen of *T. canis* larvae, E/S-antigen of *T. canis* and the combination of mTES-30 and the somatic larvae antigen revealed specificity as shown in FIG. 4c.

Measured anti-IgG antibodies may result from earlier *Toxocara* contact. The recombinant mTES-30 as well as the somatic antigen of *T. canis* larvae reveals high specificity. In this study the specificity of the E/S-antigen of *T. canis* results in lowest specificity.

CONCLUSION

The data resulting from the combination of recombinant mTES-30 and the somatic antigen of *T. canis* larvae reveals that this antigen combination allows the development of a specific test system compared to E/S-antigen based ELISA at a comparable sensitivity (FIG. 4d).

All documents cited herein, are hereby incorporated by reference in their entirety.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A carrier, comprising:
   a) a peptide comprising the amino acid sequence set forth in SEQ ID NO:1, the amino acid sequence having at least 90% identity to SEQ ID NO: 1, the amino acid sequence set forth in SEQ ID NO: 3, the amino acid sequence set forth in SEQ ID NO: 4, or a variant of SEQ ID NO: 1, wherein the variant of SEQ ID NO: 1 comprises 100% sequence identity to at least one of SEQ ID NO: 3 or SEQ ID NO: 4, wherein the peptide is immobilized to the carrier, and
   b) a somatic lysate of *Toxocara canis* larvae, wherein the somatic lysate is immobilized to the carrier.

2. The carrier according to claim 1, wherein the peptide and the somatic lysate are conjointly combined.

3. The carrier according to claim 1, wherein the carrier is selected from the group consisting of a glass slide, a biochip, a microtiter plate, a lateral flow device, a test strip, a membrane, a line blot, a chromatography column, and a bead.

4. A kit, comprising: the carrier according to claim 1, and a labeled antibody for detecting a human, Canidae or Rodentia antibody.

5. A composition, comprising:
   a) a peptide comprising the amino acid sequence set forth in SEQ ID NO:1, the amino acid sequence having at least 90% identity to SEQ ID NO: 1, the amino acid sequence set forth in SEQ ID NO: 3, the amino acid sequence set forth in SEQ ID NO: 4, or a variant of SEQ ID NO: 1, wherein the variant of SEQ ID NO: 1 comprises 100% sequence identity to at least one of SEQ ID NO: 3 or SEQ ID NO: 4, wherein the peptide comprises an artificial tag, and
   b) a somatic lysate of *Toxocara canis* larvae.

6. A method for diagnosing a *Toxocara* infection, comprising:
  detecting the *Toxocara* infection with the carrier according to claim 1.

7. A method of determining the presence of an antibody against a *Toxocara canis* protein according to SEQ ID NO:1, the amino acid sequence having at least 90% identity to SEQ ID NO: 1, the amino acid sequence set forth in SEQ ID NO: 3, the amino acid sequence set forth in SEQ ID NO: 4, a variant of SEQ ID NO: 1, wherein the variant of SEQ ID NO: 1 comprises 100% sequence identity to at least one of SEQ ID NO: 3 or SEQ ID NO: 4, and/or an antibody against a protein from a somatic lysate of *Toxocara canis* larvae, the method comprising:
  i) contacting a sample isolated from a subject having a *Toxocara* infection with a polypeptide comprising SEQ ID NO:1, the amino acid sequence having at least 90% identity to SEQ ID NO: 1, the amino acid sequence set forth in SEQ ID NO: 3, the amino acid sequence set forth in SEQ ID NO: 4, or the variant of SEQ ID NO: 1, wherein the variant of SEQ ID NO: 1 comprises 100% sequence identity to at least one of SEQ ID NO: 3 or SEQ ID NO: 4, and with the somatic lysate of *Toxocara canis* larvae, wherein the polypeptide and/or the somatic lysate binds specifically to the antibody against SEQ ID NO:1, the amino acid sequence having at least 90% identity to SEQ ID NO: 1, the amino acid sequence se forth in SEQ ID NO: 3, the amino acid sequence set forth SEQ ID NO: 4, the variant of SEQ ID NO: 1 to wherein the variant of SEQ ID NO: 1 comprises 100% sequence identity to at least one of SEQ ID NO: 3 or SEQ ID NO: 4, and/or the somatic lysate, wherein the polypeptide and the somatic lysate are immobilized to a carrier; and
  ii) determining the presence of the antibody against SEQ ID NO:1, the amino acid sequence having at least 90% identity to SEQ ID NO: 1, the amino acid sequence set forth in SEQ ID NO: 3, the amino acid sequence set forth in SEQ ID NO: 4, the variant of SEQ ID NO: 1, wherein the variant of SEQ ID NO: 1 comprises 100% sequence identity to at least one of SEQ ID NO: 3 or SEQ ID NO: 4, and/or an antibody against the somatic lysate.

8. A method, comprising:
  manufacturing a kit for detecting *Toxocara* infection, comprising:
  a) a peptide comprising the amino acid sequence set forth in SEQ ID NO:1, the amino acid sequence having at least 90% identity to SEQ ID NO: 1, the amino acid sequence set forth in SEQ ID NO: 3, the amino acid sequence set forth in SEQ ID NO: 4, or a variant of SEQ ID NO: 1, wherein the variant of SEQ ID NO: 1 comprises 100% sequence identity to at least one of SEQ ID NO: 3 or SEQ ID NO: 4, wherein the peptide s immobilized to a carrier, and
  b) a somatic lysate of *Toxocara canis* larvae, wherein the somatic lysate is immobilized to the carrier.

9. The method according to claim 6, wherein the *Toxocara* infection is distinguished from an *Echinococcus*, a *Strongyloides* and an *Ascaris* infection.

10. The method according to claim 7, wherein the peptide and the somatic lysate are conjointly combined.

11. The method according to claim 7, wherein the *Toxocara* infection is a *Toxocara canis* infection.

12. The method according to claim 7, wherein the sample is blood, serum, plasma, urine or saliva.

13. The method according to claim 8, wherein the peptide and the somatic lysate are conjointly combined.

14. The method according to claim 8, wherein the antibody against SEQ ID NO:1, the amino acid sequence having at least 90% identity to SEQ ID NO: 1, the amino acid sequence set forth in SEQ ID NO: 3, the amino acid sequence set forth in SEQ ID NO: 4, the variant of SEQ ID NO: 1, wherein the variant of SEQ ID NO: 1 comprises 100% sequence identity to at least one of SEQ ID NO: 3 or SEQ ID NO: 4, and/or the antibody against the somatic lysate is selected from the group consisting of IgG, IgA, and IgM class antibodies.

15. The method according to claim 8, wherein the detection or determination comprises a blot assay, chemiluminescence immunoassay, light scattering immunoassay, radiolabeled immunoassay, or immunofluorescence assay.

* * * * *

UNITED STATES PATENT AND TRADEMARK OFFICE
CERTIFICATE OF CORRECTION

PATENT NO. : 11,519,919 B2
APPLICATION NO. : 16/946645
DATED : December 6, 2022
INVENTOR(S) : Babett Menge et al.

It is certified that error appears in the above-identified patent and that said Letters Patent is hereby corrected as shown below:

On the Title Page

Item (56) Line 1 in the OTHER PUBLICATIONS:
"Parasitol., Int."
Should read:
--Parasitol. Int.,--;

Item (56) Line 4 in the OTHER PUBLICATIONS:
"Parasitology"
Should read:
--Parasitology,--;

Item (56) Lines 11-12 in the OTHER PUBLICATIONS:
"Application"
Should read:
--Application No.--;

Item (56) Line 20 in the OTHER PUBLICATIONS:
"Multi-epitote"
Should read:
--Multi-epitope--;

In the Specification

Column 5, Line 36:
"cans TES-30"
Should read:
--*canis* TES-30--;

Signed and Sealed this
Fourteenth Day of March, 2023

Katherine Kelly Vidal
*Director of the United States Patent and Trademark Office*

CERTIFICATE OF CORRECTION (continued)
U.S. Pat. No. 11,519,919 B2

Column 15, Line 58:
"Potters grinder"
Should read:
--Potter's grinder--;

Column 17, Line 1:
"more than 55"
Should read:
--more than 5.5--;

Column 17, Line 35:
"MIAAIVAILLCLHLSATNACATNNDCWQVCVNNVCVANNQGCNPPCVAPQ"
Should read:
--MIAAIVVLLCLHLSATNACATNNDCGIFQVCVNNVCVANNQGCNPPCVAPQ--;

Column 17, Line 46:
"NQGCNPPCNAPQVCVAPMCVAPPPAATTTAAPGVTTTRPRACPPNWTPFN"
Should read:
--NQGCNPPCVAPQVCVAPMCVAPPPAATTTAAPGVTTTRPRACPPNWTPFN--;

Column 17, Line 47:
"NNCYIASLPGRFLFNQASDWCTQMSRVVWFDQSTVGNFGSELNFVNSFAV"
Should read:
--NNCYIASLPGRFLFNQASDWCTQTGSRVVWFDQSTVGNFGSELNFVNSFAV--;

Column 17, Line 51:
"YANFLGQWDDAPCGSLFTTPQGPVCKRPL"
Should read:
--YANFLGQWDDAPCGSLFTTPQGFVCKRPL--;

Column 17, Line 58:
"(*Tavocara canis* TES-30 fragment 172 to 207 aa)"
Should read:
--(*Toxocara canis* TES-30 fragment 172 to 207 aa)--; and Column 17, Line 60:
"RPSQPDGCCGSVTCAFVNYANFLGQWDDAPCGSLF"
Should read:
--RPSQPDGCCGSNVTCAFVNYANFLGQWDDAPCGSLF--.